United States Patent [19]
Vaitekunas

[11] Patent Number: 5,957,943
[45] Date of Patent: *Sep. 28, 1999

[54] METHOD AND DEVICES FOR INCREASING ULTRASONIC EFFECTS

[75] Inventor: Jeffrey J. Vaitekunas, West Chester, Ohio

[73] Assignee: Ethicon Endo-Surgery, Inc., Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/811,704

[22] Filed: Mar. 5, 1997

[51] Int. Cl.⁶ .................................................. A61B 17/00
[52] U.S. Cl. ............................................ 606/169; 604/22
[58] Field of Search .............................. 606/1, 169, 170; 604/22, 41, 48; 607/95, 105, 154

[56] References Cited

U.S. PATENT DOCUMENTS

| | | |
|---|---|---|
| Re. 30,536 | 3/1981 | Perdreaux, Jr. . |
| 2,874,470 | 2/1959 | Richards . |
| 3,075,288 | 1/1963 | Balamuth et al. . |
| 3,076,904 | 2/1963 | Kleesattel et al. . |
| 3,213,537 | 10/1965 | Balamuth et al. . |
| 3,368,280 | 2/1968 | Fridman et al. . |
| 3,375,583 | 4/1968 | Blank et al. . |
| 3,488,851 | 1/1970 | Haydu . |
| 3,489,930 | 1/1970 | Shoh . |
| 3,518,766 | 7/1970 | Burt . |
| 3,526,036 | 9/1970 | Goof . |
| 3,526,792 | 9/1970 | Shoh . |

(List continued on next page.)

FOREIGN PATENT DOCUMENTS

| | | |
|---|---|---|
| 1098003 | 9/1977 | Canada . |
| 0 495 634 A2 | 1/1992 | European Pat. Off. . |
| 0 495 634 A3 | 1/1992 | European Pat. Off. . |
| 0 624 346 A2 | 5/1994 | European Pat. Off. . |
| 0 624 346 A3 | 5/1994 | European Pat. Off. . |
| 29 22 239 | 5/1979 | Germany . |
| 37 07 921 A1 | 3/1987 | Germany . |
| 1388002 A1 | 4/1988 | Russian Federation . |
| WO 91/13591 | 3/1991 | WIPO . |
| WO 92/02658 | 7/1991 | WIPO . |
| WO 92/14514 | 2/1992 | WIPO . |
| WO 93/14708 | 1/1993 | WIPO . |
| WO 93/16646 | 1/1993 | WIPO . |
| WO 96/29935 | 4/1996 | WIPO . |
| WO 96/34561 | 5/1996 | WIPO . |

OTHER PUBLICATIONS

Cooper LaserSonics, Inc., Ultrasonic Surgucal Aspirator NS–100 Operator Manual, 1984, pp. 12, 13, 16, 17, and 29–33.

UltraCision Incorporated, The Harmonic Scalpel® For Gynecological Surgery, Product Sheet, Sep. 1992.

UltraCision Incorporated, The Harmonic Scalpel® For General Surgery, Product Sheet, Jan. 1993.

Snowden–Pencer, Inc., Endoscopic Plastic Surgery, 1993.

UltraCision Incorporated, Harmonic Scalpel® Price List, 1995.

UltraCision Incorporated, Harmonic Scalpel® Operating Manual, Mar. 1995.

Ethicon Endo–Surgery, Inc., Ultracision CS/LCS Layout Brochure, 1996.

*Primary Examiner*—Michael Buiz
*Assistant Examiner*—William Lewis
*Attorney, Agent, or Firm*—Rockey, Milnamow & Katz, Ltd.

[57] ABSTRACT

A surgical device in accordance with the present invention includes a plurality of transducer assemblies carried by the housing and a plurality of end effectors. Each end effector is operatively coupled to one of the transducer assemblies. One method in accordance with the present invention includes the steps of providing a plurality of end effectors, each end effector being driven by a transducer assembly. The method further includes the steps of placing the end effectors in close proximity to the tissue of a patient, energizing the plurality of end effectors to vibrate at a predetermined frequency, and contacting the tissue with the end effectors.

37 Claims, 5 Drawing Sheets

U.S. PATENT DOCUMENTS

| | | |
|---|---|---|
| 3,589,012 | 6/1971 | Richman . |
| 3,589,363 | 6/1971 | Banko et al. . |
| 3,593,425 | 7/1971 | Robinson . |
| 3,636,947 | 1/1972 | Balamuth . |
| 3,645,255 | 2/1972 | Robinson . |
| 3,654,502 | 4/1972 | Carmona et al. . |
| 3,654,540 | 4/1972 | Honig et al. . |
| 3,703,037 | 11/1972 | Robinson . |
| 3,809,977 | 5/1974 | Balamuth et al. . |
| 3,930,173 | 12/1975 | Banko . |
| 3,956,826 | 5/1976 | Perdreaux, Jr. . |
| 4,156,157 | 5/1979 | Mabille . |
| 4,175,242 | 11/1979 | Kleinschmidt . |
| 4,188,952 | 2/1980 | Loschilov et al. . |
| 4,227,110 | 10/1980 | Douglas et al. . |
| 4,370,131 | 1/1983 | Banko . |
| 4,371,816 | 2/1983 | Wieser . |
| 4,406,284 | 9/1983 | Banko . |
| 4,491,132 | 1/1985 | Aikins . |
| 4,492,574 | 1/1985 | Warrin et al. . |
| 4,750,488 | 6/1988 | Wuchinich et al. . |
| 4,808,153 | 2/1989 | Parisi . |
| 4,816,018 | 3/1989 | Parisi . |
| 4,820,152 | 4/1989 | Warrin et al. . |
| 4,867,141 | 9/1989 | Nakada et al. . |
| 4,870,953 | 10/1989 | DonMichael et al. . |
| 4,897,079 | 1/1990 | Zaleski et al. . |
| 4,920,954 | 5/1990 | Alliger et al. . |
| 4,922,902 | 5/1990 | Wuchinich et al. . |
| 4,931,047 | 6/1990 | Broadwin et al. . |
| 4,936,281 | 6/1990 | Stasz . |
| 4,974,590 | 12/1990 | Saito . |
| 4,979,952 | 12/1990 | Kubota et al. . |
| 5,011,471 | 4/1991 | Miyazaki et al. . |
| 5,026,387 | 6/1991 | Thomas . |
| 5,047,043 | 9/1991 | Kubota et al. . |
| 5,057,119 | 10/1991 | Clark et al. . |
| 5,059,210 | 10/1991 | Clark et al. . |
| 5,346,502 | 9/1994 | Estabrook et al. . |
| 5,380,274 | 1/1995 | Nita . |
| 5,382,162 | 1/1995 | Sharp . |
| 5,397,269 | 3/1995 | Beaty et al. . |
| 5,416,107 | 5/1995 | Oakley et al. . |
| 5,417,672 | 5/1995 | Nita et al. . |
| 5,425,704 | 6/1995 | Sakurai et al. . |
| 5,438,554 | 8/1995 | Seyed-Bolorforosh et al. . |
| 5,449,370 | 9/1995 | Vaitekunas . |
| 5,472,447 | 12/1995 | Abrams et al. . |
| 5,507,738 | 4/1996 | Ciervo ........................................ 604/22 |
| 5,507,743 | 4/1996 | Edwards et al. . |
| 5,509,916 | 4/1996 | Taylor . |
| 5,526,815 | 6/1996 | Granz et al. . |
| 5,540,656 | 7/1996 | Pflueger et al. . |
| 5,542,917 | 8/1996 | Nita et al. . |
| 5,546,947 | 8/1996 | Yagami et al. . |
| 5,562,609 | 10/1996 | Brumbach . |
| 5,562,610 | 10/1996 | Brumbach . |
| 5,582,588 | 12/1996 | Sakurai et al. . |
| 5,606,974 | 3/1997 | Castellano et al. . |
| 5,620,479 | 4/1997 | Diederich . |
| 5,628,743 | 5/1997 | Cimino . |

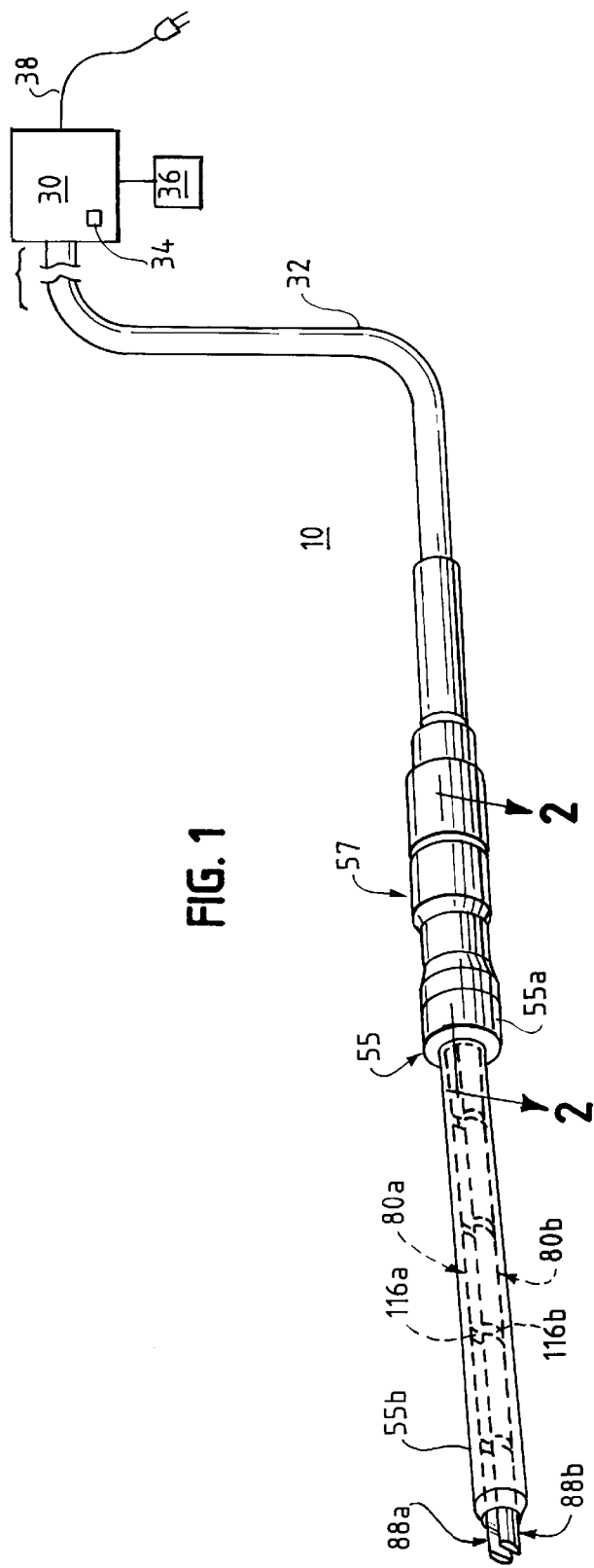
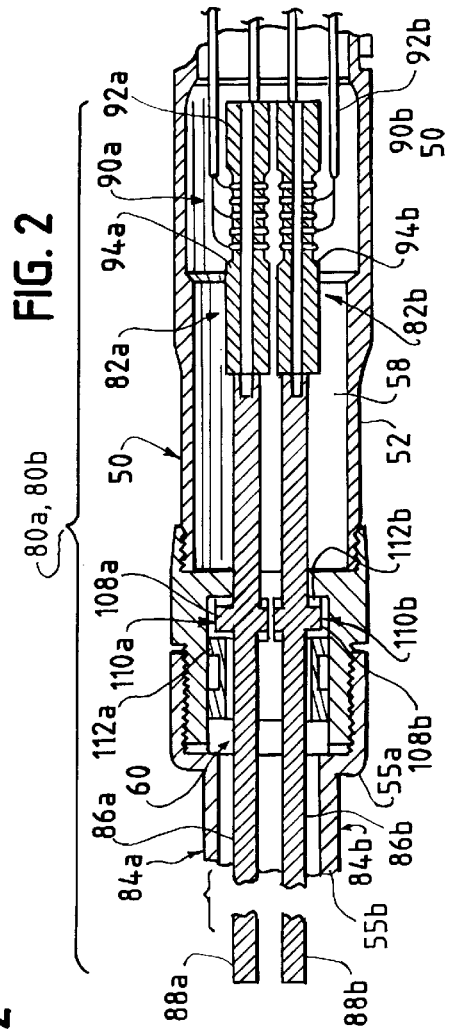
FIG. 1
FIG. 2

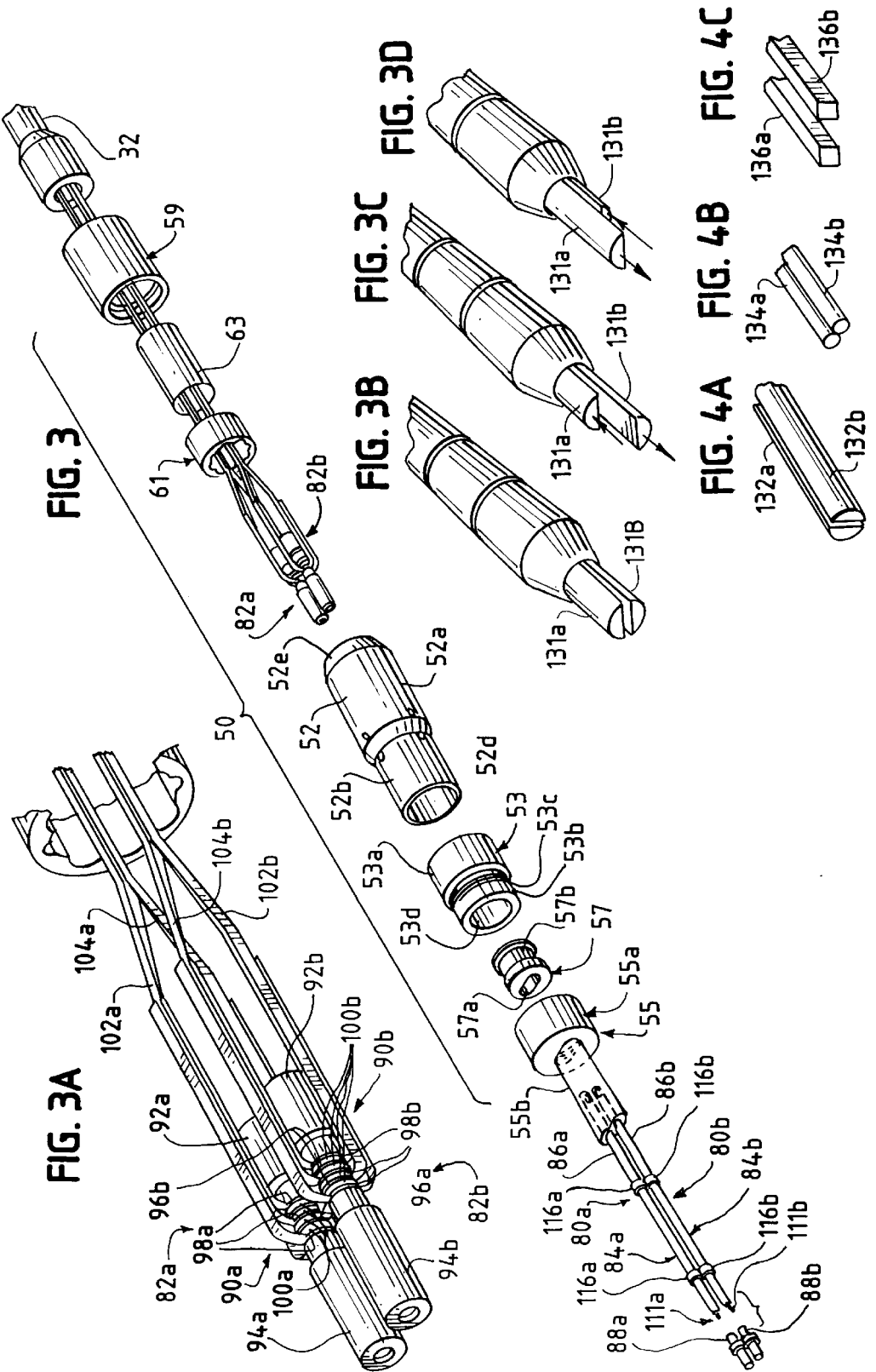

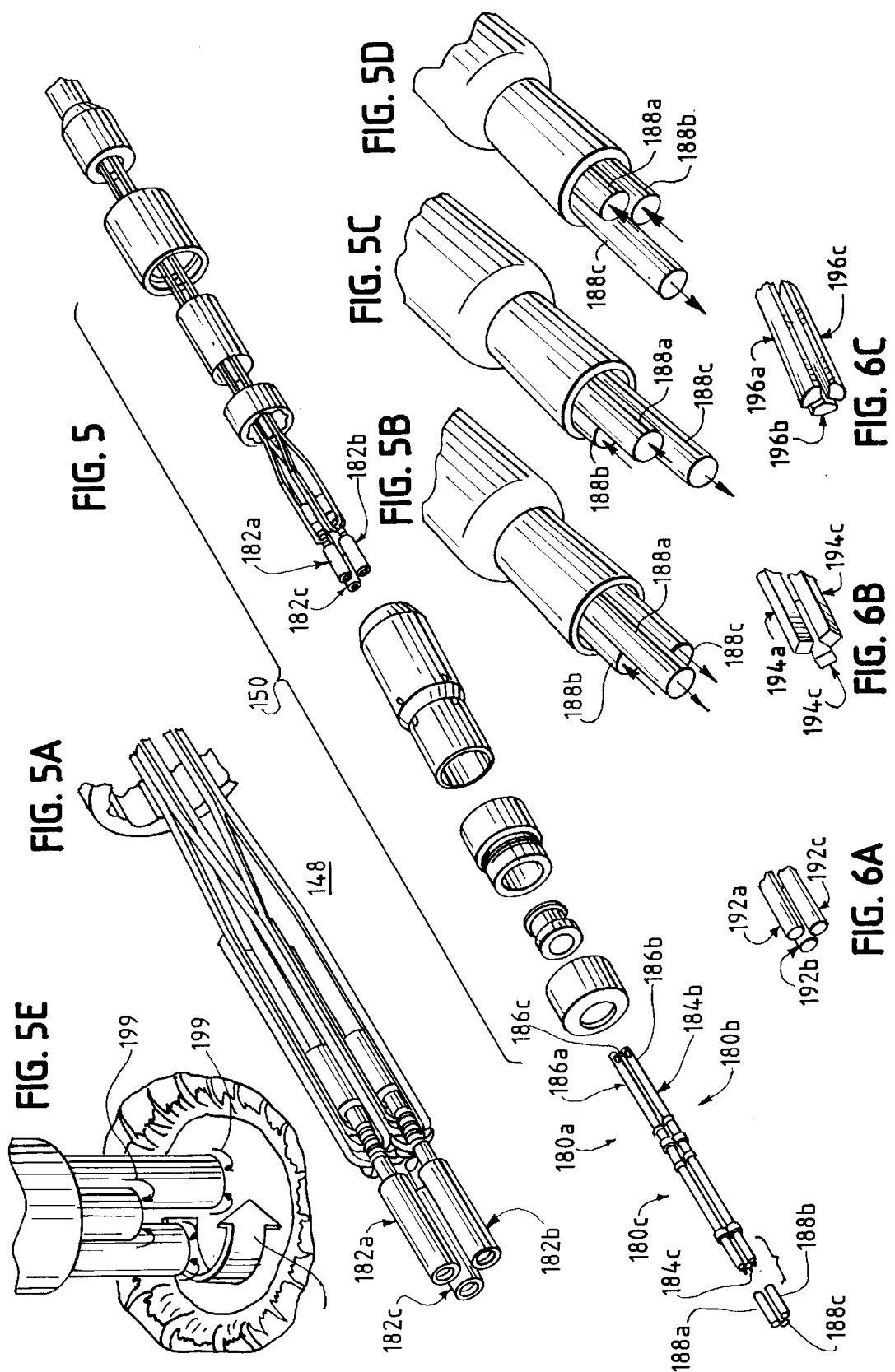

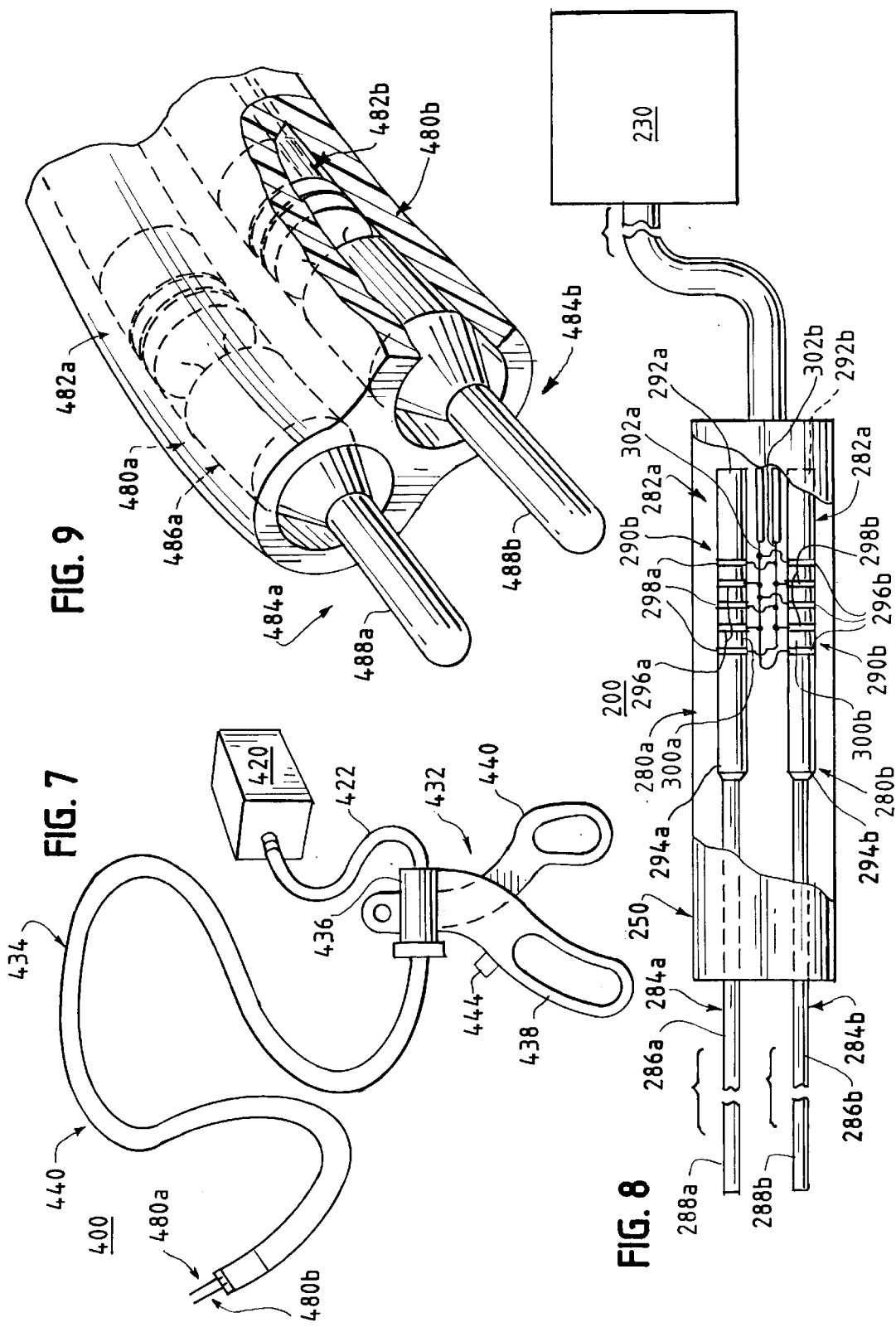

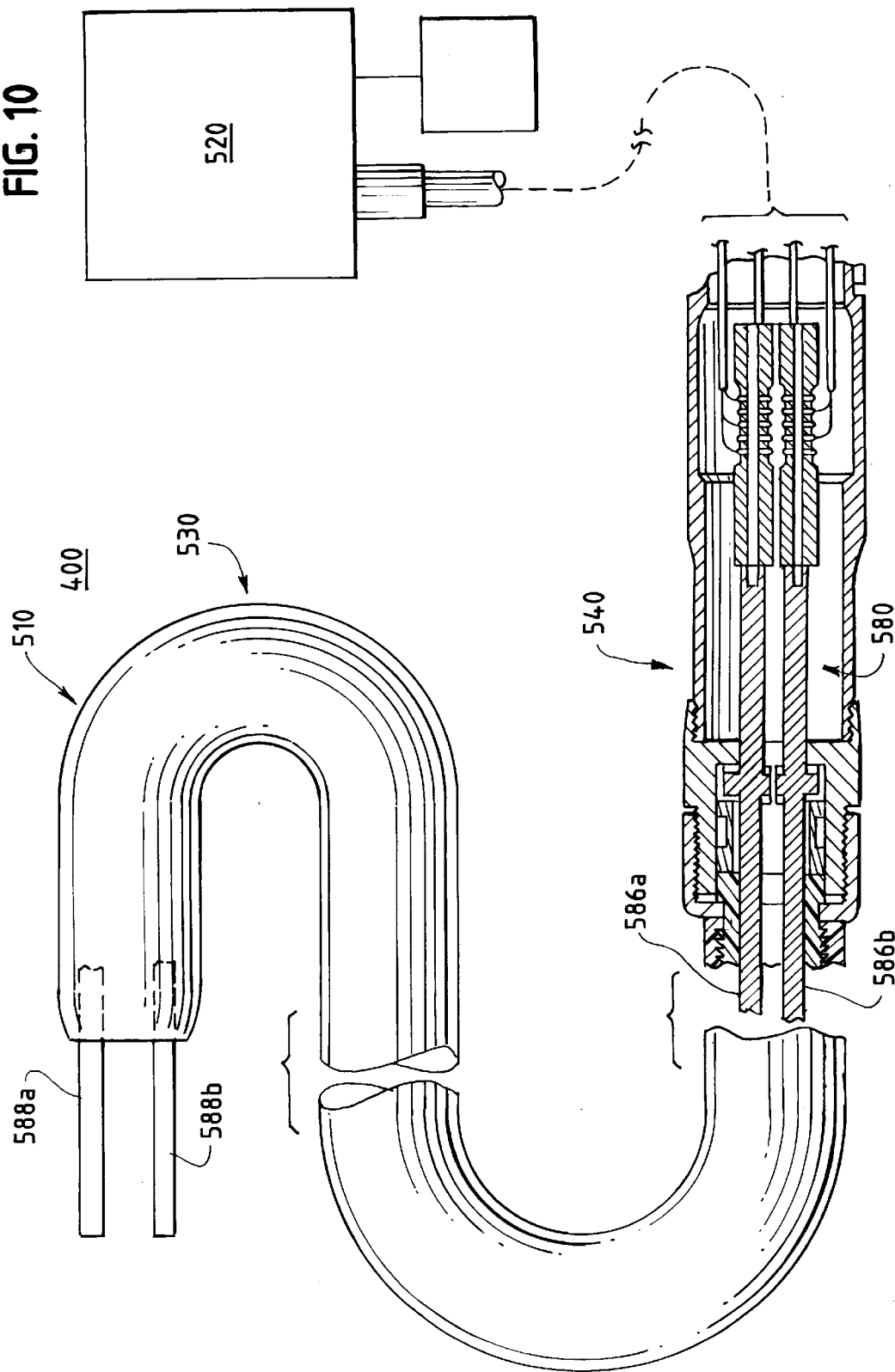

METHOD AND DEVICES FOR INCREASING ULTRASONIC EFFECTS

FIELD OF THE INVENTION

The present invention generally relates to ultrasonic transmission devices. More particularly, it relates to methods and devices having a plurality of ultrasonic transmission components to increase cavitation, microstreaming, micro-jet formation, and other ultrasonic induced activity in the material or fluid around the distal ends of the ultrasonic transmission components. The transmission components can be vibrated at the same or different frequencies, phases, and amplitudes.

BACKGROUND OF THE INVENTION

Ultrasonic transmission devices are well known for use in a variety of applications, such as in surgical operations and procedures. These transmission devices usually include a transducer that converts electrical energy into vibrational motion at ultrasonic frequencies. The vibrational motion is transmitted to vibrate a distal end of a transmission component, such as a working member. The working member may be utilized to slice, emulsify, cut, dissect, and cauterize tissue or material.

In certain surgical procedures, it is often necessary to break-up or disintegrate undesired tissue, such as tumors and plaque, within a patient's body. However, when the undesired tissue is relatively hard and dense, conventional ultrasonic devices are usually inefficient for disintegrating or breaking-up the undesired tissue into relatively small pieces. In particular, these conventional ultrasonic devices usually do not produce sufficient cavitation or micro-currents in the fluid around the distal end of the working member to break-up the undesired tissue. As a result, it can be quite difficult to remove the undesired tissues through a small lumen of a surgical instrument. In addition, a surgeon may have to alternate between surgical instruments to break-up and disintegrate tissue.

Accordingly, there is a need for methods and devices that utilize ultrasonic vibration to efficiently disintegrate and break-up undesired tissue within a patient. It would also be desirable to allow a surgeon to perform various functions or tasks with the use of a single ultrasonic device.

SUMMARY OF THE INVENTION

The present invention provides methods and devices that include a plurality of ultrasonic transmission components that disintegrate and break-up material, such as undesired tissue in a patient's body. The ultrasonic transmission components produce ultrasonic effects in the fluid or material to efficiently break-up the material. The transmission component can be vibrated at the same or different frequencies, phases, and amplitudes. The devices in accordance with the present invention are capable of producing various types of ultrasonic induced activity in the material in close proximity to the distal ends of the transmission components. For example, the transmission components may produce a circular motion in the fluid for mixing and morcellating material.

A device in accordance with the present invention includes a plurality of acoustic assemblies carried by a housing. Each acoustic assembly includes a transducer assembly and an end effector. The end effectors are adapted to vibrate at a predetermined frequency to create cavitation or other ultrasonic effects.

A method in accordance with the present invention includes the steps of providing a plurality of end effectors, each end effector being driven by a transducer assembly. The method further includes the steps of placing the end effectors in close proximity to tissue of a patient, vibrating the plurality of end effectors at a predetermined frequency, and contacting the tissue with the end effectors.

The invention, together with attendant advantages, will best be understood by reference to the following detailed description of the presently preferred embodiments of the invention, taken in conjunction with the accompanying drawings.

BRIEF DESCRIPTION OF THE DRAWINGS

FIG. 1 is a perspective view of one embodiment of a surgical system;

FIG. 2 is a fragmentary cross-sectional view of a surgical device of the surgical system about line 2—2 of FIG. 1;

FIG. 3 is an exploded perspective view of the surgical device of FIG. 2;

FIG. 3A is an enlarged perspective view of transducer assemblies of the surgical device of FIG. 3;

FIGS. 3B–3D depict the movement of the distal ends of end effectors of the surgical device of FIG. 3.

FIGS. 4A–C are fragmentary perspective views of various embodiments of the end effectors of the surgical device of FIG. 3;

FIG. 5 is an exploded perspective view of another embodiment of a surgical device;

FIG. 5A is an enlarged perspective view of transducer assemblies of the surgical device of FIG. 5;

FIGS. 5B–5D depicts the movement of the distal ends of end effectors of the surgical device of FIG. 5.

FIG 5E shows ultrasonic induced activity produced from the end effectors of FIG. 5.

FIGS. 6A–C are fragmentary perspective views of embodiments of the end effectors of the surgical device of FIG. 5;

FIG. 7 is a partial cut-away view of another embodiment of a surgical system;

FIG. 8 is a perspective view of a catheter surgical system;

FIG. 9 is a fragmentary and partially broken away view of the distal end of a catheter body of the catheter surgical system of FIG. 8; and FIG. 10 is a partial cross-sectional view of another catheter surgical system.

DESCRIPTION OF THE PREFERRED EMBODIMENTS

Before explaining the present invention in detail, it should be noted that the invention is not limited in its application or use to the details of construction and arrangement of parts illustrated in the accompanying drawings and description, because the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the invention for the convenience of the reader and are not for the purpose of limitation.

Referring now to the drawings in detail, and particularly to FIG. 1, a presently preferred embodiment of a surgical system 10 is illustrated. The surgical system 10 generally includes a generator 30, a handpiece assembly 50, and one or more acoustic or transmission assemblies 80a and 80b. The generator 30 sends electrical signals through a cable 32 at a selected amplitude, frequency, and phase determined by one or more control systems of the generator 30. As will be further described, the signals cause one or more piezoelectric elements of the acoustic assemblies 80a and 80b to expand and contract, thereby converting the electrical energy into mechanical motion. The mechanical motion results in longitudinal waves of ultrasonic energy that propagate through the acoustic assemblies 80a and 80b in an acoustic standing wave to vibrate the acoustic assemblies 80a and 80b at a selected frequency and amplitude. End effectors 88a and 88b at the distal end of the acoustic assemblies 80a and 80b are placed in close proximity or in contact with tissue of the patient to transfer the ultrasonic energy to the tissue. The cells of the tissue in contact with the end effectors 88a and 88b of the acoustic assemblies 80a and 80b will move with the end effectors 88a and 88b and vibrate.

As the end effectors 88a and 88b couple with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The end effectors 88a and 88b further enhance ultrasonic effects around the distal ends of the ends effectors 88a and 88b when they are vibrated at a selected frequency. As the end effectors 88a and 88b vibrate, cavitation is produced in the material or fluid near the distal ends of the end effectors 88a and 88b. This cavitation breaks up undesired material into fine or small particles to allow the particles to be easily removed. The end effectors 88a and 88b may be designed to influence or enhance the flow pattern in the fluid and material surrounding the distal ends of the end effectors 88a and 88b. For example, in medical applications, the end effectors 88a and 88b produce cavitation in the patient's blood, extra cellular fluid, cytoplasm, saline, or a mixture thereof to break-up undesired tissue or cells.

The ultrasonic energy also causes other effects including mechanical tearing, cutting, and emulsification. The amount of cutting as well as the degree of coagulation obtained varies with the vibrational amplitude of the end effectors 88a and 88b, the amount of pressure applied by the user, and the sharpness of the end effectors 88a and 88b. The end effectors 88a and 88b of the acoustic assemblies 80a and 80b in the surgical system 10 tend to focus the vibrational energy of the system 10 onto the tissue in contact with the end effectors 88a and 88b, intensifying and localizing thermal and mechanical energy delivery.

Referring still to FIG. 1, the generator 30 includes one or more control systems integral to generator 30, a power switch 34, and a triggering mechanism 36. The power switch 34 controls the electrical power to the generator 30, and when activated by the triggering mechanism 36, the generator 30 provides energy to drive the acoustic assemblies 80a and 80b of the surgical system 10 at a predetermined frequency and to drive the end effectors 88a and 88b at a predetermined vibrational amplitude level. The generator 30 may drive or excite the acoustic assemblies 80a and 80b at any suitable resonant frequency of the acoustic assemblies 80a and 80b.

When the generator 30 is activated via the triggering mechanism 36, electrical energy is continuously applied by the generator 30 to transducer assemblies 82a and 82b of the acoustic assemblies 80a and 80b as further shown in FIG. 2. One or more phase lock loops in the control systems of the generator 30 monitor feedback from the acoustic assemblies 80a and 80b. The phase lock loops adjust the frequency of the electrical energy sent by the generator 30 to match a preselected harmonic frequency of the acoustic assemblies 80a and 80b. In addition, one or more second feedback loops in the control systems maintain the electrical current supplied to the acoustic assemblies 80a and 80b at a preselected constant level in order to achieve substantially constant vibrational amplitude of the end effectors 88a and 88b.

The electrical signals supplied to the acoustic assemblies 80a and 80b will cause the distal ends of the end effectors 88a and 88b to vibrate longitudinally in the range of, for example, approximately 20 kHz to 200 kHz, and preferably in the range of about 54 kHz to 56 kHz, and most preferably at about 55.5 kHz. The amplitude of the acoustic vibrations at the end effectors 88a and 88b may be controlled by, for example, controlling the amplitude of the electrical signals applied to the transducer assemblies 82a and 82b of the acoustic assemblies 80a and 80b by the generator 30.

As noted above, the triggering mechanism 36 of the generator 30 allows a user to activate the generator 30 so that electrical energy may be continuously supplied to the acoustic assemblies 80a and 80b. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. It is also contemplated that two generators may be used to energize the acoustic assemblies 80a and 80b.

Referring now to FIG. 3, the handpiece assembly 50 includes a multi-piece casing adapted to isolate the operator from the vibrations of the acoustic assemblies 80a and 80b. The handpiece assembly 50 is preferably cylindrically shaped and is adapted to be held by a user in a conventional manner, but may be any suitable size and shape which allows it to be grasped by the user. The handpiece assembly 50 generally includes a housing 52, a front or nose member 53, a support member 57, a back member 59, a spacer 61, and a tubular member 63. While a multipiece handpiece assembly 50 is illustrated, the handpiece assembly 50 may comprise a single or unitary component.

The housing 52, nose member 53, support member 57, back member 59, spacer 61 and tubular member 63 of the handpiece assembly 50 may be constructed from a durable plastic, such as Ultem®. It is also contemplated that these pieces may be made from a variety of materials including other plastics (i.e. liquid crystal polymer (LCP), nylon, or polycarbonate).

The housing 52 of the handpiece assembly 50 preferably has a proximal portion 52a, a distal portion 52b, a shoulder 52c, and an axial opening 52d extending therethrough. The distal portion 52b of the housing 52 preferably has a smaller diameter than the proximal portion 52a of the housing 52. The distal portion 52b of the housing 52 is coupled or attached to the nose member 53 of the handpiece assembly 50.

The nose member 53 receives and holds the support member 57. The nose portion 53 generally includes a proximal section 53a, a distal section 53, a threaded member 53c, and an axial opening 53d. The distal section 53b of the nose portion 53 has a smaller diameter than the proximal section 53a. The distal section 53b is also configured to be threaded onto a removable sheath 55 having an adapter 55a and an elongated member 55b as further described below. As those skilled in the art will recognize, the nose member 53 may be coupled to the adapter 55a of the removable sheath 55 by any suitable means without departing from the spirit and scope of the invention.

The back member 59 of the handpiece assembly 50 is preferably coupled or secured to the proximal portion 52a of the housing 52 and is also coupled to the cable 32. The tubular member 63 and spacer 61 are preferably positioned within the handpiece assembly 50 and may support the transducer assemblies 82a and 82b.

Referring again to FIG. 2, the acoustic assemblies 80a and 80b generally include transducer stacks or assemblies 82a and 82b and transmission components or working members 84a and 84b. The transmission components 84a and 84b may include transmission rods or waveguides 86a and 86b, and end effectors or applicators 88a and 88b. The transducer assemblies 82a and 82b, transmission rods 86a and 86b, and the end effectors 88a and 88b may be acoustically tuned such that the length of each component is an integral number of one-half system wavelengths ($n\lambda/2$) where the system wavelength $\lambda$ is the wavelength of a preselected or operating longitudinal vibration frequency f of the acoustic assemblies 80a and 80b. It is also contemplated that the acoustic assemblies 80a and 80b may be any suitable arrangement of acoustic elements. For example, each acoustic assembly 80a and 80b may comprise a transducer assembly and an end effector (i.e., the acoustic assemblies 80a and 80b may be configured without transmission rods).

The transducer assemblies 82a and 82b of the acoustic assemblies 80a and 80b convert electrical signals from the generator 30 into mechanical energy that results in longitudinal vibratory motion of the end effectors 88a and 88b at ultrasonic frequencies. When the acoustic assemblies 80a and 80b are energized, a vibratory motion standing wave is generated through each acoustic assembly 80a and 80b. The amplitude of the vibratory motion at any point along the acoustic assemblies 80a and 80b depends on the location along the acoustic assemblies 80a and 80b at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda/4$).

Referring now to FIG. 3a, the transducer assemblies 82a and 82b of the acoustic assemblies 80a and 80b, which are known as "Langevin stacks," generally include transduction portions 90a and 90b, first resonators 92a and 92b, and second resonators 94a and 94b. The transducer assemblies 82a and 82b may be an integral number of one-half system wavelengths ($n\lambda/2$) in length. It is to be understood that the present invention may be alternatively configured to include transducer assemblies comprising magnetostrictive, electromagnetic or electrostatic transducers.

The distal ends of the first resonators 92a and 92b are connected to the proximal ends of transduction portions 90a and 90b, and the proximal ends of the second resonators 94a and 94b are connected to the distal ends of transduction portions 90a and 90b. The first resonators 92a and 92b and second resonators 94a and 94b are preferably fabricated from titanium, aluminum, steel, or any other suitable material. The resonators 92a, 92b, 94a and 94b have a length determined by a number of variables, including the thickness of the transduction portions 90a and 90b, the density and modulus of elasticity of material used in the resonators 92a, 92b, 94a and 94b, and the fundamental frequency of the transducer assemblies 82a and 82b. The second resonators 94a and 94b may also be tapered inwardly from their proximal ends to their distal ends to amplify the ultrasonic vibration amplitude.

The transduction portions 90a and 90b of the transducer assemblies 82a and 82b preferably comprise piezoelectric sections of alternating positive electrodes 96a and 96b and negative electrodes 98a and 98b, with piezoelectric elements 100a and 100b alternating between the electrodes 96a, 96b, 98a and 98b. The piezoelectric elements 100a and 100b may be fabricated from any suitable material, such as lead-zirconate-titanate, lead meta-niobate, lead titanate, or other ceramic piezoelectric crystal material. Each of the positive electrodes 96a and 96b, negative electrodes 98a and 98b, and piezoelectric elements 100a and 100b may have a bore extending through the center. The positive and negative electrodes 96a, 96b, 98a and 98b are electrically coupled to wires 102a, 102b, 104a and 104b, respectively. The wires 102a, 102b, 104a and 104b transmit electrical signals from the generator 30 to electrodes 96a, 96b, 98a and 98b.

The piezoelectric elements 100a and 100b are held in compression between the first resonators 92a and 92b and second resonators 94a and 94b by bolts (not shown). The bolts preferably have a head, a shank, and a threaded distal end. The bolt is inserted from the proximal end of the first resonators 92a and 92b through the bores of the first resonators 92a and 92b, the electrodes 96a, 96b, 98a and 98b, and piezoelectric elements 100a and 100b. The threaded distal ends of the bolts are screwed into threaded bores in the proximal end of second resonators 94a and 94b.

The piezoelectric elements 100a and 100b are energized in response to the electrical signals supplied from the generator 30 to produce an acoustic standing wave in each of the acoustic assemblies 80a and 80b. The electrical signals cause disturbances in the piezoelectric elements 100a and 100b in the form of repeated small displacements resulting in large compression forces within the material. The repeated small displacements cause the piezoelectric elements 100a and 100b to expand and contract in a continuous manner along the axis of the voltage producing high frequency longitudinal waves of ultrasonic energy. The ultrasonic energy is transmitted through the acoustic assemblies 80a and 80b to the end effectors 88a and 88b.

The distal ends of the second resonators 94a and 94b of the transducer assemblies 82a and 82b may be coupled to the proximal end of the transmission rods 86a and 86b by an internal threaded connection. It is contemplated that the transmission rods 86a and 86b can be attached to the transducer assemblies 82a and 82b by any suitable means. The transmission rods 86a and 86b may be coupled to the transducer assemblies 82a and 82b near an antinode. (For purposes of this disclosure, the term "near" means "exactly at" or "in close proximity to.")

The transmission rods 86a and 86b may have a length substantially equal to an integral number of one-half system wavelengths ($n\lambda/2$). The transmission rods 86a and 86b are preferably fabricated from a solid core shaft constructed out of material which propagates ultrasonic energy efficiently, such as a titanium alloy (i.e., Ti-6Al-4V) or an aluminum alloy. The transmission rods 86a and 86b may also be fabricated from any other suitable material. The transmission rods 86a and 86b may also amplify the mechanical vibrations transmitted through the transmission rods 86a and 86b to the end effectors 88a and 88b as is well known in the art.

The transmission rods 86a and 86b are connected or mounted to the handpiece assembly 50 near a node. The transmission rods 86a and 86b may also include integral rings 108a and 108b disposed around their periphery as shown in FIG. 2. The integral rings 108a and 108b are preferably disposed in annular grooves 110a and 110b formed within the handpiece assembly 50 in order to couple the transmission rods 88a and 88b to the handpiece assembly 50. Compliant members or materials 112a and 112b, such as a pair of silicone O-rings attached by stand-offs, may be placed between the annular grooves 110a and 110b to reduce or prevent ultrasonic vibration from being transmitted from the transmission rods 88a and 88b to the handpiece assembly 50.

As illustrated in FIGS. 1 and 3, the transmission rods 86a and 86b have stabilizing silicone rings or compliant supports 116a and 116b positioned near a plurality of nodes. The silicone rings 116a and 116b dampen undesirable vibration and isolate the ultrasonic energy from an elongated member of a removable sheath assuring the flow of ultrasonic energy in a longitudinal direction to the distal ends of the end effectors 88a and 88b with maximum efficiency. The silicone rings 116a and 116b may be attached together. Additional silicone rings may be located at nodes of the end effectors 88a and 88b.

As shown in FIGS. 1 and 2, a removable sheath 55 is coupled to the distal end of the handpiece assembly 50. The sheath 55 generally includes an adapter or nose cone 55a attached to an elongated member 55b having an opening extending longitudinally therethrough. The sheath 55 may be threaded or snapped onto the distal end of the handpiece assembly 50. The transmission rods 86a and 86b of the acoustic assemblies 80a and 80b extend through the elongated member 55b, and the silicone rings 116a and 116b isolate the transmission rods 86a and 86b from the elongated member 55b. The adapter 55a of the sheath 55 may be constructed from Ultem®, and the elongated member 55b may be fabricated from stainless steel. Alternatively, the transmission rods 86a and 86b may have polymeric material that surrounds the transmission rods 86a and 86b to isolate them from outside contact.

As shown in FIG. 3, the distal ends of the transmission rods 86a and 86b are adapted to be coupled to the proximal ends of the end effectors 88a and 88b by threaded connections 111a, preferably near an antinode. It is contemplated that the end effectors 88a and 88b may be attached to the transmission rods 86a and 86b by any suitable means, such as a welded joint or the like. Although the end effectors 88a and 88b may be detachable from the transmission rods 86a and 86b, it is also contemplated that the end effectors 88a and 88b and transmission rods 86a and 86b may be formed as a single unit or piece.

The end effectors 88a and 88b may have a length substantially equal to an integral multiple of one-half system wavelengths (nλ/2). The distal ends of the end effectors 88a and 88b may be disposed near an antinode in order to produce the maximum longitudinal deflection. When the transducer assemblies 82a and 82b are energized, the distal ends of the end effectors 88a and 88b are configured to move longitudinally in the range of 10 to 500 microns peak-to-peak, and preferably in the range of 30 to 100 microns at a predetermined vibrational frequency, and most preferably at about 60 microns.

The end effectors 88a and 88b may have a distal region having a smaller cross-section area than a proximal region thereof, thereby forming a vibrational amplitude step-up junction. The step-up junction acts as velocity transformer as known in the art, increasing the magnitude of the ultrasonic vibration transmitted from the proximal region to the distal region of the end effectors 88a and 88b.

The end effectors 88a and 88b are preferably made from a solid core shaft constructed of material which propagates ultrasonic energy, such as a titanium alloy (i.e., Ti-6Al-4V) or an aluminum alloy. The end effectors 88a and 88b may be fabricated from any other suitable material. It is also contemplated that the end effectors 88a and 88b may have a surface treatment to improve the delivery of energy and desired tissue effect. For example, the end effectors 88a and 88b may be micro-finished, coated, plated, etched, grit-blasted, roughened or scored to enhance coagulation in tissue. Additionally, the end effectors 88a and 88b may be sharpened or shaped to enhance its energy transmission characteristics. For example, the end effectors 88a and 88b may be blade shaped, hook shaped, or ball shaped.

Referring now to FIGS. 3B–3D, the ultrasonic motion of end effectors 188a and 188b of a surgical system is illustrated. It will be recognized that the motion of the end effectors is exaggerated for purposes of describing this embodiment. Each of the end effectors 188a and 188b may vibrate at a predetermined amplitude and frequency. The end effectors 188a and 188b are configured to enhance or amplify cavitation to create a back and forth sawing motion of the micro-currents in the fluid around the end effectors. The end effectors 188a and 188b may be vibrated at 0° to 180° out of phase to produce desired cavitation. As shown in FIGS. 3C, the end effector 188a may be retracting while the end effector 188b is extending, and, at a later point in time, the end effector 188a may be extending while the end effector 188b is retracting as shown in FIG. 3D. It is contemplated that the end effectors may be vibrated at the same or different frequencies, phases, and amplitudes.

Referring now to FIGS. 4A–C, fragmentary perspective views of a number of embodiments of end effectors of the surgical system 10 are illustrated. As shown in FIG. 4A, end effectors 132a and 132b have a substantially semi-circular cross-section. With this configuration, the end effectors 132a and 132b can enhance cutting, emulsification, and coagulation, and provide maximal distal surface area for a given tip diameter. In FIG. 4B, end effectors 134a and 134b have a substantially circular cross-section. With this configuration, the end effectors 134a and 134b can be of a less expensive construction, have higher vibrational amplitudes, and be subject to fewer unwanted vibrations. In FIG. 4C, end effectors 136a and 136b have a substantially square cross-section. With this arrangement, the circumferential edges of the square cross-section of the end effectors 136a and 136b can increase cutting. The distal ends of the end effectors 136a and 136b may also have, for example, a recessed tip, or the end effectors may have an opening extending therethrough to remove material. It is contemplated that the configurations of the end effectors may be any suitable shape for different applications without departing from the spirit and scope of the present invention.

Referring now to FIG. 5, another preferred embodiment of a surgical device 148 is illustrated. The surgical device 148 generally includes a handpiece assembly 150 and acoustic assemblies 180a, 180b, 180c. The acoustic assemblies 180a, 180b, 180c include transducer assemblies 182a, 182b, 182c and transmission components or working members 184a, 184b, 184c. The acoustic assemblies 180a, 180b, 180c are carried by the handpiece assembly 150. It is contemplated that any number of acoustic assemblies, for example, such as 2 to 6, may be carried by the handpiece assembly 150 without departing from the spirit and scope of the invention. The acoustic assemblies 180a, 180b and 180c each preferably have transducer assemblies 182a, 182b and 182c (see FIG. 5A), transmission rods 186a, 186b and 186c, and end effectors or applicators 188a, 188b and 188c, respectively. The construction of the handpiece assembly 150 and the acoustic assemblies 180a, 180b, 180c are substantially similar to the handpiece assembly and acoustic assemblies described above. As such, further description of the handpiece assembly 150 and acoustic assemblies 180a, 180b, 180c are unnecessary for a complete understanding of this embodiment.

As shown in FIGS. 5B–5D, the movement of end effectors 188a, 188b, 188c of the surgical device 148 is illustrated. As the end effectors 188a, 188b and 188c vibrate, cavitation may be produced by the displacement of the end effectors 188a, 188b, 188c. This cavitation destroys and breaks-up material into small or tiny particles by mixing and morcellating the material. The end effectors 188a, 188b, 188c are configured to enhance microstreaming by producing circular, vortex-like micro-currents around the end effectors as shown by arrows 198 and 199 in FIG. 5E. The end effectors 188a, 188b, 188c may be vibrated with the same or different phase. It is also contemplated that the end effectors 192a, 192b, 192c may be vibrated at different frequencies, amplitudes, and phases.

Referring now to FIGS. 6A–C, a number of embodiments of the end effectors of the surgical device 148 are illustrated. The end effectors are configured to vibrate at a predetermined frequency and amplitude. As shown in FIG. 6A, the end effectors 192a, 192b, 192c each have a substantially circular cross-section. With this arrangement, the end effectors 192a, 192b, 192c can be of a less expensive construction, have higher vibrational amplitudes, and be subject to fewer unwanted vibrations. As shown in FIG. 6B, the end effectors 194a, 194b, 194c have a substantially square cross-section. With this configuration, the circumferential edges of the square cross-section of the end effectors 194a, 194b, 194c can increase cutting. In FIG. 6C, the end effectors 196a, 196b, 196c have a cross-sectional shape formed by two radii and an arc (i.e., a partial-section of a circle). It is contemplated that the end effector configurations may be any suitable shape for different applications without departing from the spirit and scope of the invention.

Referring now to FIG. 7, another preferred embodiment of an ultrasonic system 200, having a pair of transducers electrically coupled to two wires extending through a cable, is illustrated. The ultrasonic system 200 generally includes a generator 230, handpiece assembly 250, and acoustic or transmission assemblies 280a and 280b. The handpiece assembly 250 and generator 230 are substantially similar to the generator and handpiece assembly described above. As such, further description of the generator 230 and handpiece assembly 250 are unnecessary for a complete understanding of this embodiment.

The acoustic assemblies 280a and 280b of the surgical device 200 generally include transducer assemblies 282a and 282b and working members or transmission components 284a and 284b. The working members 284a and 284b preferably include transmission rods 286a and 286b, and end effectors or applicators 288a and 288b.

The transducer assemblies 282a and 282b of the acoustic assemblies 280a and 280b, which are known as "Langevin stacks," generally include transduction portions 290a and 290b, first resonators 292a and 292b, and second resonators 294a and 294b. The transducer assemblies 282a and 282b may be an integral number of one-half system wavelengths (nλ/2) in length. It is to be understood that the present invention may be alternatively configured to include transducer assemblies comprising magnetostrictive, electromagnetic or electrostatic transducers.

The distal ends of the first resonators 292a and 292b are connected to the transduction portions 290a and 290b, and the proximal ends of the second resonators 294a and 294b are connected to the transduction portions 290a and 290b. The first resonators 292a and 292b and second resonators 294a and 294b are preferably fabricated from titanium, aluminum, steel, or any other suitable material. The second resonators 294a and 294b may each be tapered inwardly from its proximal end to its distal end to amplify the ultrasonic vibration amplitude.

The transduction portions 290a and 290b of the transducer assemblies 282a and 282b preferably comprise piezoelectric sections of alternating positive electrodes 296a and 296b and negative electrodes 298a and 298b, with piezoelectric elements 300a and 300b alternating between the electrodes 296a, 296b, 298a and 298b. The piezoelectric elements 300a and 300b may be fabricated from any suitable material, such as lead-zirconate-titanate, lead meta-niobate, lead titanate, or other ceramic piezoelectric crystal material. Each of the positive electrodes 296a and 296b, negative electrodes 298a and 298b, and piezoelectric elements 300a and 300b may have a bore extending through the center. The positive and negative electrodes 296a, 296b, 298a and 298b are electrically coupled to wires 302a and 302b that transmit electrical signals from the generator 230.

The piezoelectric elements 300a and 300b are held in compression between the first resonators 292a and 292b and second resonators 294a and 294b by a bolt (not shown). The bolt preferably has a head, a shank, and a threaded distal end. The bolt is inserted from the proximal end of the first resonators 292a and 292b through the bores of the first resonators 292a and 292b, the electrodes 296a, 296b, 298a and 298b and piezoelectric elements 300a and 300b. The threaded distal end of the bolt is screwed into a threaded bore in the proximal end of second resonators 294a and 294b.

The connection between the wires 302a and 302b and the positive electrodes 296a and 296b and the negative electrodes 298a and 298b of the transducer assemblies 282a and 282b are preferably alternated. As shown in FIG. 7, the wire 302a is connected to the end electrodes and the middle electrode of the transducer assembly 282a and connected to the two electrodes adjacent to the middle electrode of the transducer assembly 282b. The wire 302b is connected to the two end electrodes and the middle electrode of the transducer assembly 282b and connected to the two electrodes adjacent to the middle electrode of the transducer assembly 282a. As a result, the piezoelectric elements of the transducer assembly 282a will have an opposite polarity of the respective piezoelectric elements of the transducer assembly 282b. Accordingly, when the transducer assemblies 282a and 282b are energized, the end effectors 288a and 288b will have 180° phase difference. It is also contemplated that the direction of piezoelectric elements in one of the transducers may be changed (i.e., the piezoelectric elements may be turned 180°) instead of alternating the connection of the wires with the electrodes. As a result, when the signal is positive, the piezoelectric elements in one transducer assembly will expand, while the crystals in the other transducer will contract resulting in the end effectors having a 180° phase difference.

Referring now to FIG. 8, another preferred embodiment of a catheter surgical system 400 is illustrated. The surgical system 400 can break-up and disintegrate materials and tissue within a cardiovascular system of a patient. The surgical system 400 generally includes a generator 420, a probe or catheter assembly 440, and a plurality of acoustic assemblies 480a and 480b. The surgical system 400 may have any suitable number of acoustic assemblies 480a and 480b. The generator 420 is substantially similar to the generators described above. As such, further description of the generator 420 is unnecessary for a complete understanding of present invention.

The probe assembly 440 generally includes a handle 432 and a catheter body 434. The handle 432 is configured to allow the probe assembly 440 to be easily grasped and held by a physician in order to allow the catheter body 434 to be manipulated within the patient. The handle 432 preferably includes a housing 436, a finger grip 438, and a thumb grip 440. The distal end of the housing 436 is coupled to the proximal end of the catheter body 434 and the proximal end of the housing 436 is coupled to the generator 420 by a cable 422.

The housing 436, finger grip 438, and thumb grip 440 are preferably constructed from a durable plastic, such as Ultem®. It is also contemplated that these components made from a variety of materials including other plastics (i.e. liquid crystal polymer (LCP), nylon, or polycarbonate).

In one embodiment, a switch 444 may be incorporated into the finger grip 438 of the handle 434 to allow the generator 420 to be activated by a user. Alternatively, a foot activity switch may be coupled to the generator 420 by a cable or cord to allow a user or surgeon to activate the generator 420.

The catheter body 434 of the probe assembly 430 is configured to be inserted into the vascular system of a patient from an entrance site, e.g. a femoral artery or vein. Preferably, the catheter body includes a steerable catheter. The catheter body 434 may be made from a variety of materials including polyurethane, silicone rubber, or any other suitable material commonly used in conventional catheters.

A guide wire may be inserted in a guide wire passage of the catheter body 434 so that the guide wire may be longitudinally advanced or retracted through the distal end of the catheter body 434. A fluid lumen may also extend through the catheter body 434 to transmit a flushing fluid or to apply suction to the distal end of the catheter body 434 to clear fluids and debris from an area adjacent to the distal end.

The acoustic assemblies 480a and 480b of the surgical system 400 are preferably disposed near the distal end of the catheter body 434. As shown in FIG. 9, the acoustic assemblies 480a and 480b are each positioned within a respective lumen of the catheter body 434. The acoustic assemblies 480a and 480b generally include transducer stacks or assemblies 482a and 482b and working members or transmission components 484a and 484b. The working members 484a and 484b preferably include end effectors or applicators 488a and 488b. The transducer assemblies 482a and 482b and end effectors 488a and 488b may be acoustically tuned such that the length of each component is an integral number of one-half wavelengths (n$\lambda$/2). It is also contemplated that the acoustic assemblies 480a and 480b may be any suitable arrangement of acoustic elements. For example, the acoustic assemblies 480a and 480b may comprise transducer assemblies, transmission rods and end effectors as described above.

The transducer assemblies 482a and 482b are operatively coupled to the generator 420 via one or more wires. The transducer assemblies 482a and 482b are substantially similar to the transducer assemblies described above except that they are reduced in size, may have a fewer number of piezoelectric elements, and may have a tapered second resonator. As such, further description of the transducer assemblies 482a and 482b is unnecessary for a complete understanding of the invention. It is also contemplated that the transducer assemblies 482a and 482b may be alternatively configured to include magnetostrictive, electromagnetic, or electrostatic transducers.

A plurality of seals (not shown) may be distributed along the lumen of the catheter body 434 to support the transducer assemblies 482a and 482b. The seals may be fabricated from silicone to isolate the catheter body 434 from the transducer assemblies 482a and 482b. As those skilled in the art will recognize, the transducer assemblies 482a and 482b may be supported by any suitable means.

The distal ends of the transducer assemblies 482a and 482b are preferably coupled to the proximal end of the end effectors 488a and 488b by an internal threaded connection near an antinode. The end effectors 488a and 488b are preferably fabricated from a titanium alloy, such as Ti-6Al-4V. It is contemplated that the end effectors 488a and 488b may be manufactured from any suitable material without departing from the spirit and scope of the invention.

The end effectors 488a and 488b may have a length of an integral multiple of half wavelengths (n$\lambda$/2) in order to produce the maximum longitudinal deflection at its remote end. The end effectors 488a and 488b may have a diameter of about 0.1–5 mm, and, preferably, a diameter of about 0.5–2 mm, and, most preferably, a diameter of 1 mm. It is contemplated that the end effectors 488a and 488b may also include a velocity transformer or amplifier.

The catheter body 434 may be routed into the cardiovascular system of a patient. After the catheter body 434 has been inserted and positioned in a vessel of the patient, the user may activate the ultrasonic transmission device to cause the end effectors 488a and 488b of the acoustic assemblies to vibrate. When the end effectors 488a and 488b are vibrated, the end effectors 488a and 488b can disintegrate and break-up material or tissue.

Referring now to FIG. 10, another embodiment of a catheter surgical system 500 is illustrated. The surgical system 500 includes an ultrasonic transmission device 510 and a generator 520. The ultrasonic transmission device 510 preferably includes a catheter body 530, a handpiece assembly 540, and a plurality of acoustic assemblies 550a and 550b disposed within the handpiece assembly 540. It is contemplated that the ultrasonic device 510 may include any suitable number of acoustic assemblies.

The generator 520 is substantially similar to the generator described above. As such, further description of the generator 520 is unnecessary for a complete understanding of this embodiment.

The catheter body 530 of the ultrasonic transmission device 510 includes a proximal end, a distal end, and one or more lumens extending therethrough (not shown). As illustrated in FIG. 10, the handpiece assembly 540 is preferably coupled to the proximal end of the catheter body 530. The handpiece assembly 540 is substantially similar to the handpiece assemblies described above. Accordingly, further description of the handpiece assembly 540 is unnecessary for a complete understanding of this embodiment.

The acoustic assemblies 550a and 550b are substantially the same as the acoustic assemblies described above except that the transmission rods 586a and 586b are flexible. The acoustic assemblies may be constructed from titanium (Ti-6Al-4V), Nitinol (NiTi) or any suitable material. In one embodiment, the transmission rod 586a and 586b may have a diameter in the range of 0.5 mm–5 mm, and end effectors 588a and 588b have a diameter in the range of about 0.1 mm–5 mm. The transmission rods 586a and 586b and end effectors 588a and 588b preferably have a diameter of about 0.5 mm–2 mm. Most preferably, the transmission rods 586a and 586b have a diameter of 0.5 mm and the end effectors 588a and 588b have a diameter of 1 mm. It is contemplated that the transmission rods 586a and 586b and end effectors 588a and 588b may be any suitable diameter.

The catheter body 530 is preferably flexible to allow the catheter 530 to be manipulated and slid through a lumen or vessel of a patient. The catheter 530 may be fabricated from any suitable medical grade material and may be fabricated in various sizes depending on the size of the vessel that is desired to be negotiated with the catheter body 530. Preferably, the catheter body 530 includes a steerable catheter.

The catheter body 530 may be routed into the cardiovascular system of a patient. After the catheter body 530 has been inserted and positioned in a vessel of the patient, the user may activate the ultrasonic transmission device to cause end effectors of the acoustic assemblies to vibrate. When the end effectors are vibrated, the end effectors can break-up and disintegrate material or tissue.

The catheter body 530 may be visually monitored by the physician using fiber optics or may be viewed by ultrasound imaging or fluoroscopic imaging. The catheter body 530 may also use a guide wire to initially position the distal end of the catheter body 530 in a desired area in the patient.

The devices and methods of the present invention include a plurality of transmission components to increase ultrasonic effects in order to disintegrate and break-up material. The devices produce cavitation in the fluid around distal ends of acoustic assemblies to efficiently break-up and disintegrate material. The devices can produce various types of motion or cavitation around the distal end, such as a circular motion or a sawing motion. The devices in accordance with the present invention may be inserted through an incision or a port in a patient, or may be inserted into the vascular system of a patient. Additionally, the devices may be used in a variety of other surgical applications wherein a treatment site is accessed via a natural or surgical lumen or incision, including, for example, joints, cavities, organs, spaces, tumors, etc.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical device comprising:
    a first transducer assembly adapted to vibrate at an ultrasonic frequency in response to electrical energy;
    a second transducer assembly adapted to vibrate at an ultrasonic frequency in response to electrical energy;
    a first transmission rod having a first end and a second end, the first transmission rod being coupled to and adapted to receive the ultrasonic vibration from the first transducer assembly and to transmit the ultrasonic vibration from the first end to the second end of the first transmission rod, the first end of the first transmission rod being coupled to the first transducer assembly; and
    a second transmission rod having a first end and a second end, the second transmission rod being coupled to and adapted to receive the ultrasonic vibration from the first transducer assembly and to transmit the ultrasonic vibration from the first end to the second end of the second transmission rod, the first end of the second transmission rod being coupled to the second transducer assembly; and
    a first end effector having a first end and a second end, the first end effector being adapted to receive the ultrasonic vibrations from the first transmission rod and to transmit the vibration from the first end to the second end of the first end effector, the first end of the first end effector being coupled to the second end of the transmission rod, the second end of the first end effector disposed; and
    a second end effector having a first end and a second end, the second end effector being adapted to receive the ultrasonic vibration from the second transmission rod and to transmit the vibration from the first end to the second end of the second end effector, the first end of the second end effector being coupled to the second end of the transmission rod, the second end of the second end effector being disposed near an antinode.

2. The device of claim 1 wherein the first end effector is vibrated at a different frequency than the second end effector.

3. The device of claim 1 wherein the first end effector is vibrated 180° out of phase with the second end effector.

4. The device of claim 1 further comprising a generator to energize the first and second transducer assemblies.

5. An ultrasonic surgical device comprising:
    a first transducer assembly adapted to vibrate at an ultrasonic frequency in response to electrical energy;
    a second transducer assembly adapted to vibrate at an ultrasonic frequency in response to electrical energy;
    a first transmission component having a first end and a second end, the first transmission component being adapted to receive the ultrasonic vibration from the first transducer assembly and to transmit the ultrasonic vibration from the first end to the second end of the first transmission component; and
    a second transmission component having a first end and a second end, the second transmission component being adapted to receive the ultrasonic vibration from the second transducer assembly and to transmit the ultrasonic vibration from the first end to the second end of the second transmission component,
    said first and second transmission components being respectively coupled to said first and second transducer assemblies.

6. The device of claim 5 wherein at least one of the acoustic assemblies has a substantially circular cross-section.

7. The device of claim 5 wherein at least one of the acoustic assemblies has a substantially semi-circular cross-section.

8. The device of claim 5 wherein at least one of the acoustic assemblies has a substantially square cross-section.

9. The device of claim 5 further including a generator to energize the transducer assemblies.

10. The device of claim 5 wherein the first and second transmission components are operated independently of one another.

11. The device of claim 5 wherein the first and second transmission components are adapted to vibrate at different frequencies.

12. The device of claim 5 wherein the first transmission component vibrates 180° out of phase with the second transmission component.

13. A surgical device comprising:
  a housing carrying a first transducer assembly and a second transducer assembly;
  the first and second transducers each including a plurality of piezoelectric elements;
  a first end effector adapted to receive ultrasonic vibrations from the first transducer assembly; and
  a second end effector adapted to receive ultrasonic vibrations from the second transducer.

14. The device of claim 13 wherein the piezoelectric elements of the first transducer have opposite polarity of the respective piezoelectric elements of the second transducer assembly.

15. The device of claim 13 wherein the first and second transducer assemblies each have four piezoelectric elements.

16. The device of claim 13 wherein the piezoelectric elements of the first transducer assembly have the opposite polarity of the piezoelectric elements of the second transducer assembly.

17. The device of claim 13 wherein the first end effector vibrates 180° out of phase with the second end effector.

18. A surgical device comprising:
  a first transducer assembly adapted to vibrate at an ultrasonic frequency in response to electrical energy;
  a second transducer assembly adapted to vibrate at an ultrasonic frequency in response to electrical energy;
  a first transmission wire having a first end and a second end, the first transmission wire having the first end thereof coupled to said first transducer assembly to receive ultrasonic vibration from the first transducer assembly and to transmit the ultrasonic vibration from the first end to the second end of the first transmission wire; and
  a second transmission wire having a first end and a second end, the second transmission wire having the first end thereof coupled to said second transducer assembly to receive ultrasonic vibration from the second transducer assembly and to transmit the ultrasonic vibration from the first end to the second end of the second transmission wire.

19. The surgical device of claim 18 further comprising
  a first end effector having a first end and a second end, the end effector being adapted to receive the ultrasonic vibration from the first transmission wire and to transmit the ultrasonic vibration from the first end to the second end of the first end effector; and
  a second end effector having a first end and a second end, the second end effector adapted to receive the ultrasonic vibration from the second transmission wire and to transmit the ultrasonic vibration from the first end to the second end of the second end effectors.

20. The device of claim 19 wherein the first and second end effector have a diameter between 0.1 mm and 5 mm.

21. The device of claim 19 wherein the transmission wire extends through a lumen of a catheter.

22. The device of claim 19 further comprising a generator to send electrical energy to the transducer assemblies.

23. A method of producing ultrasonic effects to tissue of a patient comprising the steps of:
  providing a plurality of end effectors, each end effector being driven by a respective transducer assembly;
  placing the end effectors in close proximity to the tissue of a patient;
  vibrating the plurality of end effectors at a predetermined frequency; and
  contacting the tissue with the end effectors.

24. A method of producing ultrasonic effects to tissue of a patient comprising the steps of:
  providing a plurality of end effectors and a plurality of transducer assemblies, each said end effector being driven by a respective one of said transducer assemblies;
  placing the end effectors in close proximity to the tissue of a patient;
  vibrating each of the plurality of end effectors at a respective predetermined frequency by operation of the respective one of said transducer assemblies; and
  contacting the tissue with the end effectors.

25. The method of claim 24 further repeating the steps of advancing, dissecting and withdrawing.

26. An ultrasonic surgical device comprising:
  a housing;
  first and second transducer assemblies carried by the housing, the transducer assemblies adapted to vibrate at an ultrasonic frequency in response to electrical energy;
  a catheter body couplable to the housing, the catheter body having a first end, a second end and at least one lumen extending longitudinally therethrough, the catheter body configured to be placed within a vessel of a patient's vascular system;
  first and second flexible transmission rods extending longitudinally through the catheter, the first and second transmission rods having a first end and a second end, the first and second transmission rods adapted to receive ultrasonic vibration from the first and second transducer assemblies, respectively, and to transmit the ultrasonic vibration from the first end to the second end of each transmission rod; and
  a first and second end effector coupled to the second ends of the first and second transmission rods, respectively, the first and second end effector adapted to receive the ultrasonic vibration from the first and second transmission rods, respectively, and to transmit the vibrations from a first end to a second end of the end effectors wherein the first and second end effectors are extendable beyond the second end of the catheter to contact the tissue.

27. A surgical device comprising:
  a catheter defining a lumen;
  a plurality of transducer assemblies carried by the catheter and positioned therein along a lengthwise dimension of the catheter; and
  a plurality of end effectors, each end effector being coupled to a respective one of the transducer assemblies for ultrasonically driving said end effectors, said end effectors extending distally relative to the transducer assemblies, each end effector having a vibrating distal end extending distally of a distal end of said catheter.

28. The surgical device of claim 27, wherein said transducer assemblies are positioned generally at a proximal portion of said catheter, said device including a plurality of flexible transmission components extending through said lumen and coupling each said end effector to the respective one of said transducer assemblies.

29. The surgical device of claim 27, wherein said transducer assemblies are positioned generally at a distal portion of said catheter.

30. A method of breaking up tissue comprising the steps of:

providing a surgical device including a plurality of acoustic assemblies, each having a transducer assembly and an end effector coupled to the respective transducer assembly;

energizing the surgical device to cause the end effectors of the acoustic assemblies to vibrate; and contacting the end effectors of the acoustic assemblies with tissue of a patient.

31. The method of claim 30, wherein said energizing step includes vibrating said end effectors out of phase with each other.

32. A surgical device comprising:

a housing which carries a plurality of end effectors, each said end effector extending from a distal end of said housing;

the plurality of end effectors being operable at the same or different ultrasonic frequencies, phases, or amplitudes by transmission of ultrasonic energy thereto for performing a surgical procedure.

33. The surgical device of claim 32, wherein said housing comprises a catheter.

34. An ultrasonic surgical device comprising:

a first transducer assembly adapted to vibrate at an ultrasonic frequency in response to electrical energy;

a second transducer assembly adapted to vibrate at an ultrasonic frequency in response to electrical energy;

a generator to energize the first and second transducer assemblies;

a first transmission rod having a first end and a second end, the first transmission rod being adapted to receive the ultrasonic vibration from the first transducer assembly and to transmit the ultrasonic vibration from the first end to the second end of the first transmission rod, the first end of the first transmission rod being coupled to the first transducer assembly;

a second transmission rod having a first end and a second end, the second transmission rod being adapted to receive the ultrasonic vibration from the first transducer assembly and to transmit the ultrasonic vibration from the first end to the second end of the second transmission rod, the first end of the second transmission rod being coupled to the second transducer assembly;

a first end effector having a first end and a second end, the first end effector being adapted to receive the ultrasonic vibrations from the first transmission rod and to transmit the vibration from the first end to the second end of the first end effector, the first end of the first end effector being coupled to the second end of the transmission rod, the second end of the first end effector disposed; and a second end effector having a first end and a second end, the second end effector being adapted to receive the ultrasonic vibration from the second transmission rod and to transmit the vibration from the first end to the second end of the second end effector, the first end of the second end effector being coupled to the second end of the transmission rod, the second end of the second end effector being disposed near an antinode.

35. The device of claim 34, wherein the first end effector is vibrated out of phase with the second end effector.

36. An ultrasonic surgical device comprising:

a first transducer assembly adapted to vibrate at an ultrasonic frequency in response to electrical energy;

a second transducer assembly adapted to vibrate at an ultrasonic frequency in response to electrical energy;

a first transmission component having a first end and a second end, the first transmission component being adapted to receive the ultrasonic vibration from the first transducer assembly and to transmit the ultrasonic vibration from the first end to the second end of the first transmission component;

a second transmission component having a first end and a second end, the second transmission component being adapted to receive the ultrasonic vibration from the second transducer assembly and to transmit the ultrasonic vibration from the first end to the second end of the second transmission component; and a third transducer assembly adapted to vibrate at an ultrasonic frequency in response to electrical energy; and a third transmission component having a first end and a second end, the third transmission component adapted to receive ultrasonic vibration from the third transducer assembly and to transmit the ultrasonic vibration from the first end to the second end of the third transmission component.

37. A method of breaking up tissue within a patient's body comprising the steps of:

inserting a catheter having a plurality of end effectors, each driven by a transducer assembly, in a cardiovascular system of the patient;

advancing the catheter through the cardiovascular system until a desired area is reached;

vibrating the distal ends of the end effectors;

directing the end effectors into a position in close proximity with the tissue;

withdrawing the end effectors from the tissue; and repeating the steps of advancing, directing and withdrawing.

* * * * *